United States Patent [19]
Losch et al.

[11] Patent Number: 4,722,337
[45] Date of Patent: Feb. 2, 1988

[54] MEDICAL LASER PERIPHERALS AND CONNECTOR SYSTEM

[75] Inventors: Richard C. Losch, Union City; Peter Hertzmann, Palo Alto, both of Calif.

[73] Assignee: Laserscope, Santa Clara, Calif.

[21] Appl. No.: 849,486

[22] Filed: Apr. 7, 1986

Related U.S. Application Data

[63] Continuation-in-part of Ser. No. 525,833, Aug. 22, 1983, Pat. No. 4,580,557.

[51] Int. Cl.⁴ .............................................. A61B 17/36
[52] U.S. Cl. ........................... 128/303.1; 128/395; 219/121 LA; 219/121 LZ
[58] Field of Search ............... 128/303.1, 395–398; 219/121 LA, 121 LZ

[56] References Cited

U.S. PATENT DOCUMENTS

| | | | |
|---|---|---|---|
| 3,487,835 | 9/1963 | Koester et al. | 128/303.1 |
| 3,865,113 | 2/1975 | Sharon et al. | 128/303.1 |
| 4,091,814 | 5/1978 | Togo | 128/303.1 |
| 4,122,853 | 10/1978 | Smith | 128/303.1 |
| 4,215,694 | 8/1980 | Isakov | 128/303.1 |
| 4,580,557 | 4/1986 | Hertzmann | 128/303.1 |

FOREIGN PATENT DOCUMENTS 75912 4/1983 European Pat. Off.
3105297 12/1981 Fed. Rep. of Germany.

Primary Examiner—Lee S. Cohen
Attorney, Agent, or Firm—Ciotti, Murashige, Irell, Manella

[57] ABSTRACT

An improved configuration for interchangeable laser surgery peripheral devices is disclosed. This configuration, which is an improved embodiment of the configuration disclosed in U.S. Ser. No. 525,833, includes a directional plug of predetermined fixed orientation adapted to be connected to a laser output device. Within this plug and extending therefrom is an axially centered, flexible, laser light transmissive elongated optic fiber, the plug end of which is aligned to receive the output of the laser and the distal end of which is to be used for effecting the laser surgery procedure. The plug, when connected to the laser output in its predetermined fixed orientation provides an unambiguous signature signal which distinguishes the particular peripheral device from the other interchangeable peripheral devices. This connector system has the advantage of minimizing the cost of the signature generating parts within the peripheral device and facilitating the fabricating of inexpensive disposable peripheral devices. In another of the invention a laser energy resistive ceramic is used to align and affix the optic fiber into the plug.

16 Claims, 11 Drawing Figures

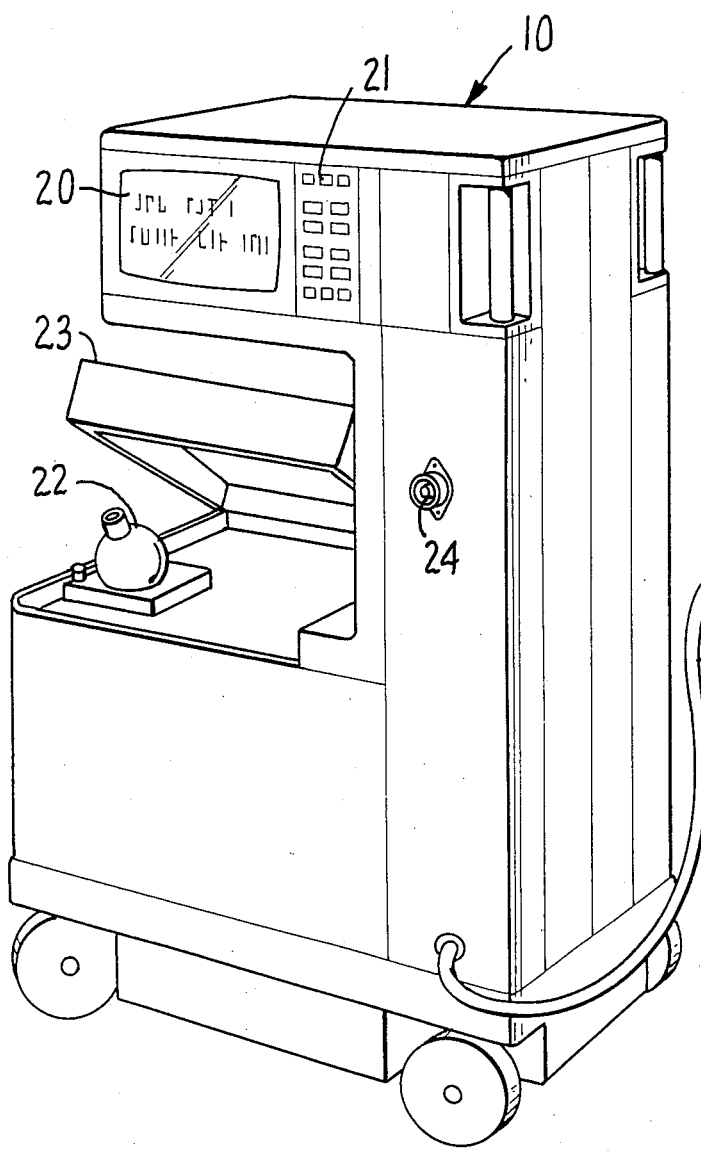
FIG. 1.
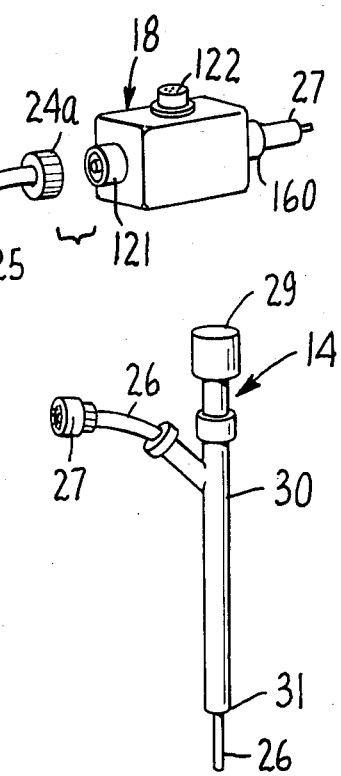
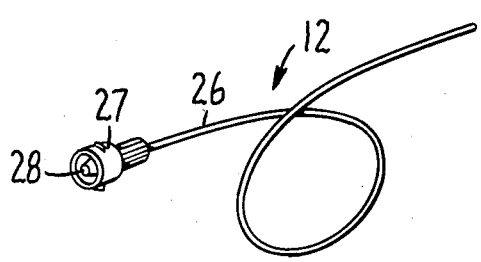
FIG. 1A.
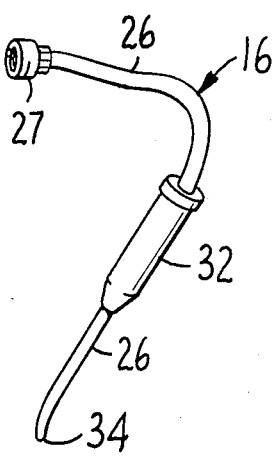
FIG. 1C.

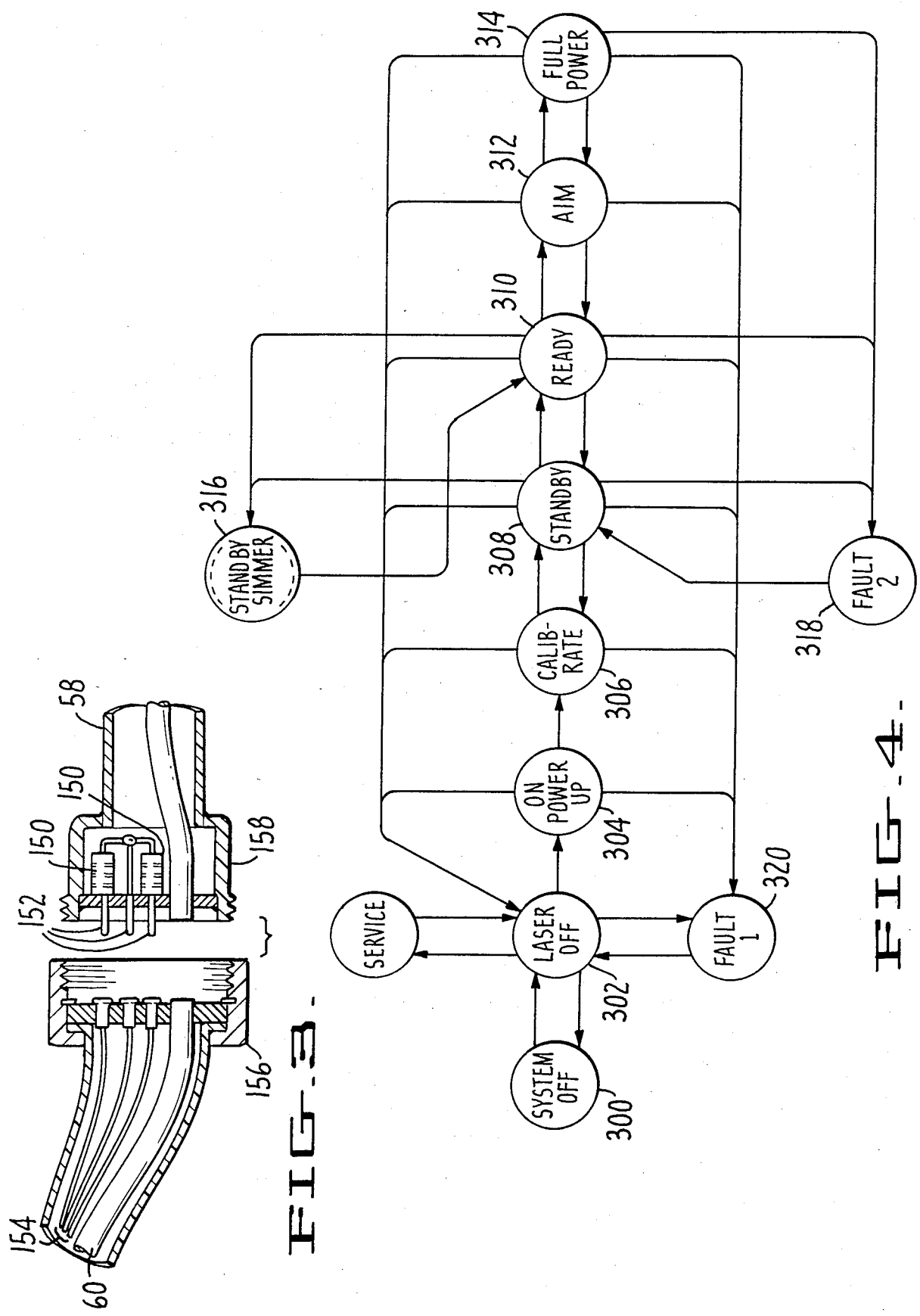

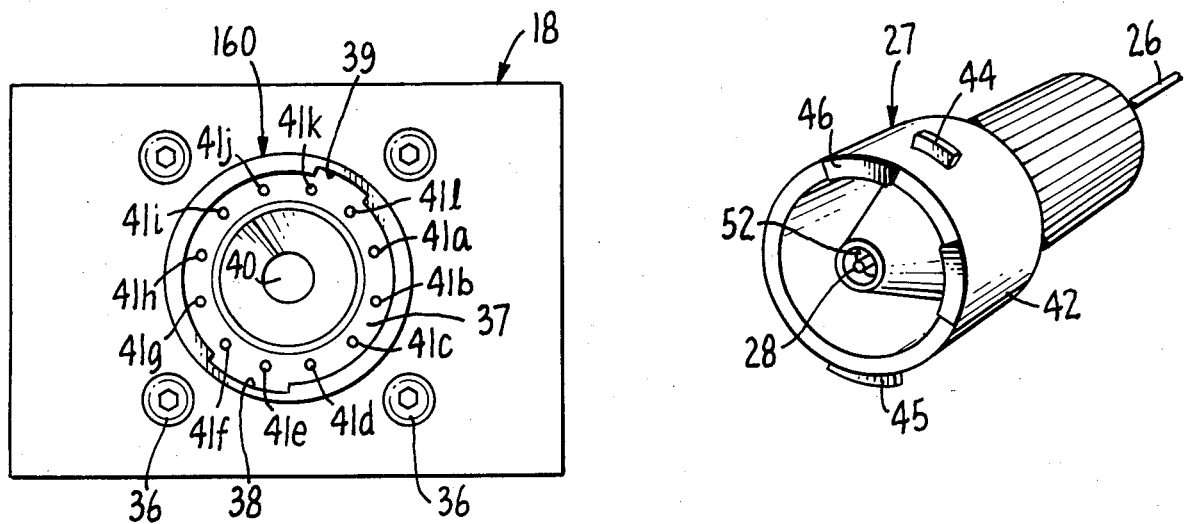
FIG.5
FIG.6
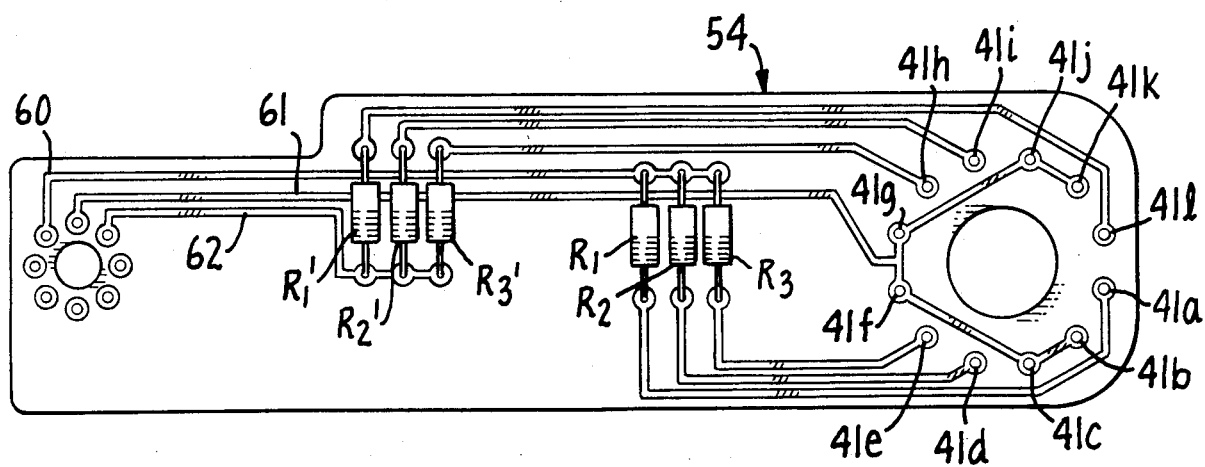
FIG.7

MEDICAL LASER PERIPHERALS AND CONNECTOR SYSTEM

The application is a continuation-in-part of pending U.S. patent application Ser. No. 525,833, filed Aug. 22, 1983, now U.S. Pat. No. 4,580,557.

BACKGROUND OF THE INVENTION

1. Field of the Invention

This invention is in the field of medical equipment. More particularly it concerns a connector system for coupling laser output to medical or surgical peripheral devices and the peripherals themselves.

2. Reference to Related Application

This application is related to U.S. patent application Ser. No. 525,833 filed on Aug. 22, 1983 and to issue on Apr. 8, 1986. That application is incorporated herein by reference.

3. Description of Prior Art

Surgical techniques employing laser radiation have been in development for several years. Laser beam manipulator devices have been employed as surgical scalpels as illustrated in, for example, U.S. Pat. No. 3,865,113 of Sharon et al; European Patent Application Ser. No. 75,912 (Published Apr. 6, 1983) of Hitachi, Ltd.; and West German Pat. No. 3105297 of Asaki Kogaku Kogyo. Laser devices can also be used to effect blood coagulation or to cauterize as shown by, for example, U.S. Pat. No. 3,487,835 of Koester et al. Laser surgical devices may be macroscale or may be sized for operation under a microscope to perform microsurgery as is described in, for example, U.S. Pat. No. 4,091,814 of Togo. As emphasized in related application U.S. Ser. No. 525,833, these various techniques have created a need for medical laser systems having varied power levels and peripheral attachments, so that a single laser may be used in performing these various techniques.

It is necessary to precisely control the amount of laser radiation delivered to biological tissues in photo-surgical procedures. The appropriate amount of radiation is known to vary with the technique employed. Systems have been developed to control the intensity and duration of the laser radiation energy applied to the treated tissues. See U.S. Pat. No. 4,215,694 of Isakov et al; U.S. Pat. No. 4,122,853 of Smith; as well as previously noted U.S. Ser. No. 525,833 and EPO Patent Application No. 75,912. Systems such as the Smith system rely on exposure control devices such as shutters and laser power level control circuits.

The difficulty of controlling the amount of laser radiation delivered to tissues is aggravated when various peripheral devices, having varying optical properties and power requirements, are used in the same system. It is essential that the laser output be correctly matched to the peripheral device. Preferably, the laser and peripheral should be connected in a way which absolutely precludes a mismatch.

U.S. Ser. No. 525,833 shows a laser system in which each of variety of peripheral devices had a "signature" which could be read by the remainder of the laser system to identify the peripheral device and distinguish it from all other such devices. Such peripheral devices are now claimed. In the preferred embodiment shown by that patent application the signature was created by preselected electrical resistances built into the peripheral device itself which were read by the control circuit of the laser system.

While this prior preferred embodiment has proven very effective, it has one drawback. There are applications where it is convenient to have the peripheral devices in a disposable form. Since the resistors are located in the peripheral device, they would be discarded with it. It is expensive and at times difficult to obtain signature resistors of such precision that they give a proper and unabiguous signature with every replaceable peripheral.

This invention, in addition to these earlier-disclosed signature peripherals, provides improved peripherals and a coupling system for the laser which provides an unambiguous signature and facilitates use of disposable peripheral laser surgical implements.

SUMMARY OF THE INVENTION

An improved configuration for interchangeable laser surgery peripheral devices has now been found. This configuration, which is an improved embodiment of the configuration disclosed in U.S. Ser. No. 525,833, includes a directional plug of predetermined fixed orientation adapted to be connected to a laser output device. Within this plug and extending therefrom is an axially centered, flexible, laser light transmissive elongated optic fiber, the plug end of which is aligned to receive the output of the laser and the distal end of which is to be used for effecting the laser surgery procedure. The plug, when connected to the laser output in its predetermined fixed orientation provides an unambiguous signature signal which distinguishes the particular peripheral device from the other interchangeable peripheral devices. In preferred aspects, the signature signal is an electrical signal, more preferably a signal generated by a circuit created when the plug provides means to bridge contacts within the laser output device, or within an optical coupler which itself may contain the signature-generating devices. This preferred embodiment has the advantage of minimizing the cost of the signature generating parts within the peripheral device and facilitating the fabrication of inexpensive disposable peripheral devices because expensive resistors and the like are contained in the laser itself or in the optical coupler and not in the peripherals. In further preferred aspects, this invention additionally employs a laser energy resistive ceramic to affix the optic fiber in the plug and insulate the plug (which is commonly made of thermoplastic) to protect it from excessive heat.

BRIEF DESCRIPTION OF THE DRAWINGS

FIG. 1 is a sectional view of a medical laser system console.

FIGS. 1A, 1B and 1C are pictorial views of examples of interchangeable surgical peripheral devices of this invention usable with such a laser.

FIG. 3 is a detail of FIG. 2 showing the construction of connector portions of a peripheral surgical device and a cable emanating from the system console.

FIG. 4 is a schematic illustration of modes of operation of the control circuitry of a laser system useful with the present invention.

FIG. 5 is a front view of a socket assembly for coupling a laser in accord with preferred aspects of this invention.

FIG. 6 is a perspective view of a plug for so coupling a laser.

FIG. 7 is a schematic of one representative electrical circuit for creating a signature for a laser peripheral.

DETAILED DESCRIPTION OF THE INVENTION

Figure 2:
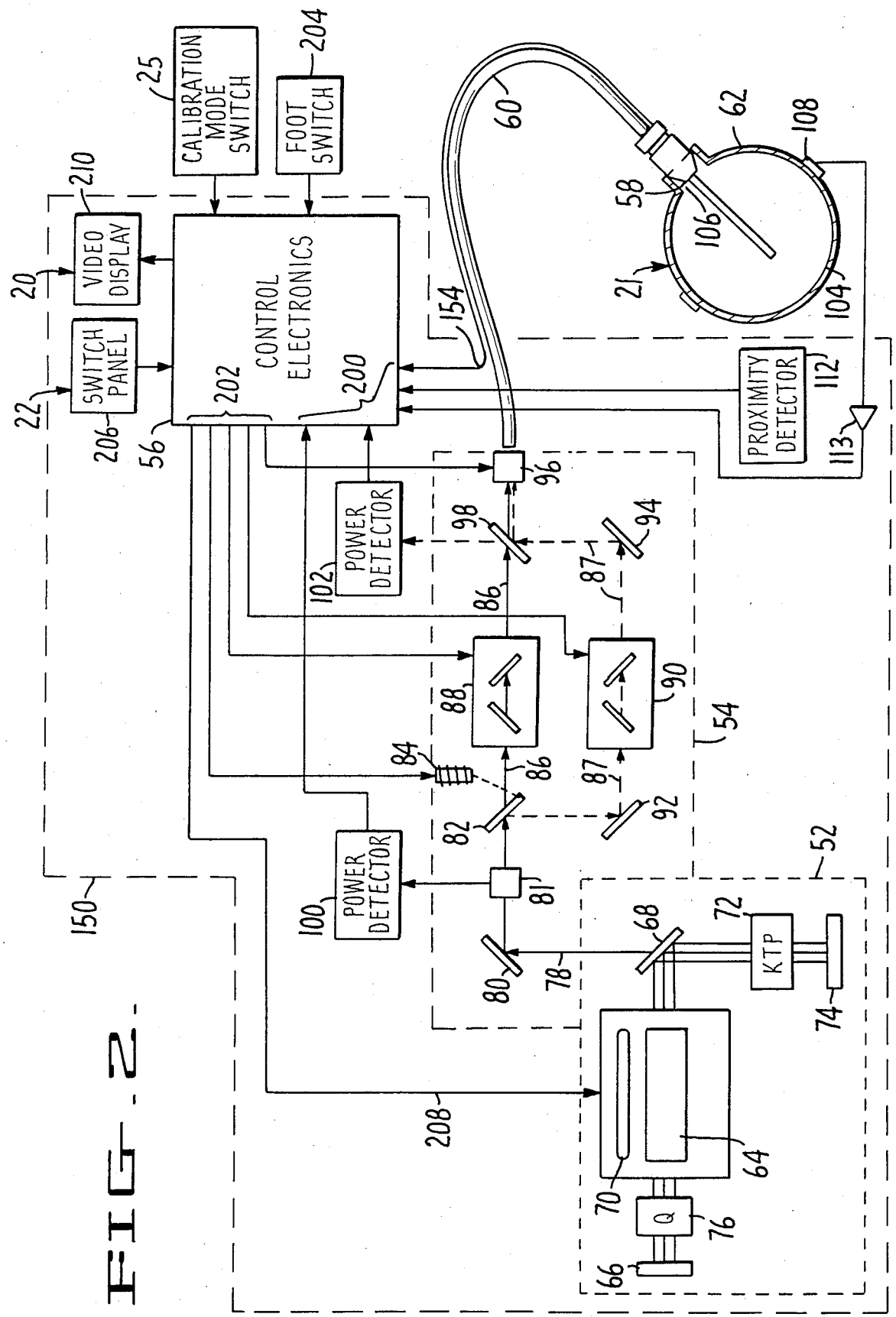
FIG. 2 is a schematic diagram of an embodiment of the optical and electrical elements employed in the a system useful with the present invention.

Referring first to FIGS. 1, 1A, 1B and 1C, a medical laser system is illustrated including a laser console 10, an optical/electrical coupler 18 and several exemplary peripheral surgical devices 12, 14, and 16. The peripheral surgical devices are adapted to be selectively coupled to the laser output. The laser console 10 may include an optical system consisting of a laser, directing and attenuating devices, and control electronics which are not shown. The console may include a video display 20 and input key pad 21 by which the operation of the system may be manually monitored and controlled, for example, by reading on display 20 the identity of the attached peripheral device and by entering via pad 21 power output set points suitable for the particular surgical technique and peripheral devices in use. The laser console may also include other associated elements such as a calibration pod 22 stored under a lid 23. Peripheral surgery devices are coupled to the laser console, for example via connector socket 24 or socket 24A and conductor 25, and preferably through optical coupler 18.

The exemplary peripheral surgical devices shown in FIGS. 1A through 1C include a generic laser energy transmissive fiber optic device 12 for supplying laser energy to surgical appliances. Device 12 includes a laser light transmissive fiber optic 26 attached to coupling plug 27. Fiber optic 26 is axially aligned in plug 27 such that its end 28 can receive the output of the laser in console 10 when it is attached to socket 24 or 24A, especially through the optical/electrical coupler 18. As will be described below in detail, plug 27 and socket 24 cooperate when joined to provide a signature signal to the control circuits of the laser in console 10. Another exemplary peripheral surgical device shown is the laser endoscope 14, which include an eye piece 29 and optical system 30 for viewing the surgical operation performed through a catheter portion 31 of the device. This device includes a fiber optic 26 and connector 27 as just described. The third exemplary periphery surgical device 16 is a laser scalpel having a shank portion 32 for manual manipulation and an output tip 34 through which laser light supplied through fiber 26 and connector 27 may be directed to tissues for the purpose of cutting the tissues. It should be understood that the examples of peripheral surgical devices shown in FIG. 1 are not exhaustive. Such devices may also include dermal handpieces, microsurgical scalpels, microsurgical handpieces, intraocular probes, rhinal probes, microcautery probes, macrocautery probes, endoscopic probes, laser microscopic device, and other laser-powered medical devices known in the prior art. They may also include cautery probes and scalpels having tip portions heated by laser radiation, wherein the laser light does not impinge on the tissues.

In operation, the control circuit may be employed to identify the peripheral surgical device by means of a device signature, enable the apparatus to produce a laser output from the surgical device when the surgical device is coupled to the radiation sensor 22 for calibration, and disable the apparatus from producing a laser output for surgical use until the laser output of the surgical device has been calibrated.

When plug 27 is inserted into optical/electrical coupler 18 it not only couples the laser output to the peripheral device, it also generates a unique indicia of identity or "signature" for the peripheral device which the laser control circuit can "read" and display or otherwise use.

FIG. 2 is a schematic diagram of an embodiment of the optical and electrical elements employed in the surgical laser system of the present invention. The portion of the apparatus which may be enclosed within the console 10 of FIG. 1 is surrounded by the dotted line 50. The apparatus may include a laser 52, a beam directing and attenuating optical system 54 and control circuitry 56. Laser radiation may be coupled to a peripheral surgical device 58 by means of a optical fiber cable 60. A calibration pod or calibration radiation sensor may be connected to the console 10.

In operation the control circuit may be employed to identify the peripheral surgical device by means of a device signature, enable the apparatus to produce a radiation output from the surgical device when the surgical device is coupled to the radiation sensor 21 for calibration, and disable the apparatus from producing a radiation output for surgical use unitl the radiation output of the surgical device has been calibrated.

The details of the constructions of the apparatus of FIG. 2 will now be described in detail.

The laser 52 may, advantageously, be a frequency doubled YAG laser. Such a laser is capable of providing relatively high power levels at a frequency or wavelenght such that readily available, flexible optical fiber cables may be used to couple the laser radiation to the peripheral surgical device. Such a system may employ a Nd:YAG (Neodymium-doped yttrium aluminum garnet) laser rod 64 located between an end mirror 66 and a laser output mirror 68. The rod may be pumped by a single laser pump lamp 70. A KTP ($KTiOPO_4$) frequency doubling crystal 72 may be employed at the required power levels to achieve frequency doubling. As shown, the KTP crystal 72 is located between an end mirror 74 and the laser output mirror 68. An acoustoptical O switch 76 may be provided to selectively quench the laser action to control the laser output. In operation the laser may be capable of produing up to 20 watts of laser radiation at a wavelength of about 532 nanometers. These output parameters make the system highly flexible and adaptable to use with a variety of peripheral medical devices.

An output laser beam 78 from the laser 52 may be coupled to the beam directing and attenuating optical system 54. The beam directing and attenuating optical system 54 may include an input beam splitter and folding mirror 80 and a selectively positionable beam splitter 82 controlled by a solenoid 84. The selectively positionable beam splitter 82 provides for the selective production of a main power beam (indicated by the solid arrows 86), or a lower power aiming beam (indicated by the dotted arrows 87). Conventional rotating polarized attenuators 88 and 90 may be placed in the path of the main power beam and the aiming beam, reflectively. The power of the laser radiation in the aiming beam may be reduced by lossy aiming beam relfectors 92 and 94. The main power beam or the aiming beam may be directed on a shutter 96 by means of beam splitter and folding mirror 98. When the shutter 96 is open, the power beam or aiming beam may be coupled to the optical fiber cable 60.

In operation, before the laser beam from the laser 52 enters the optical fiber cable 60, a small portion of the beam may be sampled by a beam splitter 81 and measured by a power detector 100, which is employed to measure the average output power of the laser 52. When the beam splitter 82 is moved out of the path of the laser beam, the laser beam passes to the main beam attenuator 88, which consists of two polarizing plates. Because the output beam of the laser is polarized, a rotation of the plane of incidence of the polarizing plates will attenuate the beam to a selective degree determined by the degree of rotation of the attenuator. A small motor (not shown) may be used to rotate the attenuator to produce any desired degree of attenuation. The two polarizing attenuating plates are used so that the lateral offset of the beam due to one plate is compensated by second plate. Consequently, as the attenuator is rotated, the output beam remains on axis.

Following the main beam attenuator, the main beam impinges on the beam splitter 98. A portion of the beam is directed to the second power detector 102. Ths detector monitors the power of the laser beam just before it enters the optical fiber cable 60.

The electromechanical shutter 96 is employed to block the beam on command, and is located between the beam splitter 98 and the optical fiber cable 60.

A parallel, lower power, aiming beam may be selectively derived from the output beam of the laser 52 and attenuated in a fashion similar to the main power beam just described. To produce the aiming beam the beam splitter 82 may be positioned by the solenoid 84 in the location shown in FIG. 2 to direct the laser beam toward the lossy reflector 92. From the lossy reflector 92 the aiming beam may be directed into the aiming beam attenuation 90, which operates in a fashion similar to the main power beam attenuator 88, previously described. The aiming beam may then be reflected off of lossy reflector 94 into the beam splitter 98. As in the main power beam, an average output power level of the aiming beam may be detected by the power detector 102.

The calibration pod or sensor 21 such as those known in the prior art, may be provided to calibrate the peripheral surgical devices which are selectively attached to the system. In the preferred embodiment shown in FIG. 2, the calibration sensor 21 consists of an integrating sphere 104 having an aperture 106 through which the peripheral surgical device may be inserted or its output beam directed, and a light sensitive electronic device such as a light sensitive silicon diode 108 located in a wall of the sphere. The inside surface of the sphere may be a diffusing surface as sand-blasted metal, anodized aluminum or magnesium sulfate. At any point on the surface of the sphere, the amount of illumination is essentially constant and insensitive to the exact positioning of the peripheral surgical device 58 with respect to the senosr.

Advantageously, the calibration sensor 21 may be removable from the console 10 and this removal detected by a proximity detector 112 which causes the system to enter its calibration mode.

As discussed above, many different peripheral surgical tools may be employed with this system. Such tools may be selectively coupled to the optical fiber cable 60. FIG. 3 is a detail of FIG. 2 showing the construction of connector portions of a peripheral surgical device and a cable emanating from the system console. The detail also illustrates the construction and function of signature resistors which may be employed in a preferred embodiment of the present invention to identify a particular peripheral surgical devices in use.

In one embodiment of the present invention, signature resistors 150 may be located in a portion of peripheral surgical device 58 and provided with electrical contacts 152 by which the signature resistors are selectively connected to the control circuitry 56. The peripheral surgical device 58 may be coupled to the optical fiber cable and to a control circuitry cable 154 by means of a releasable coupling such as the threaded coupling sleeves 156 and 158 shown in FIG. 3. When a shank portion of the peripheral surgical device 58 is inserted in the coupling, the optical fiber cable 60 is optically coupled to the surgical device 58 and the signature resistors 150 are coupled to the control circuitry. The resistances of the signature resistors may be detected by the control circuitry, and the peripheral surgical device identified on the basis of these detected resistance. In alternative embodiments an end of the optical fiber cable from the laser may be coupled to an end of an optical fiber cable leading to the surgical device by a conventional optical coupler which focuses light from one optical fiber cable end to the other.

With continued reference to FIG. 2 the operation of the control circuitry will now be described. The control circuitry 56 may include a general purpose digital computer or special purpose microcomputer, as well as, appropriate conventional analog-to-digital and digital-to-analog converters. The control circuitry 56 receives information concerning the operation of the system from the data inputs grouped at location 200, and from a foot switch 204, the calibration mode switch 25 and switch panel 22. Control signal outputs from the control circuitry are grouped at location 202.

In operation a peripheral surgical device 58 may be selected for calibration and surgical use. The eral surgical device 58 may be coupled to the optical fiber cable 60 and electrical cable 154. The signature resistors in the peripheral surgical device 58 may then be interrogated to determine the identity of that particular surgical device.

The control circuitry will block the production of a laser beam by the laser optical system until the peripheral device is calibrated. The system may be switched to a calibration mode by removing the calibration sensor 21 from the console. A signal from the proximity detector 112 may be employed to trigger the control circuitry to enter a calibration mode.

The peripheral surgical device 58 may then be inserted into the sensor. The calibration mode switch 25 may be pressed to activate the control circuitry. At this point, a low power laser radiation pulse is produced by the system and coupled into the peripheral surgical device 58. The radiation output of the device 58 is detected by the sensor 21 and a signal representative of the power of the output beam of the peripheral surgical device 58 is communicated to the control circuitry via amplifier 113. At about the same time, power detectors 100 and 102 may produce signals representative in value of the power levels measured from the beams provided to those power detectors by the beam splitters 80 and 98. The control electronics 56 may then calculate a value representative of the ratio between the output power levels sensed by the power detectors 100 and/or 102, and the actual output power of the peripheral surgical device 58 as measured by the calibration sensor 21. This value may be stored for further use in an electronic memory.

When this process has been performed, the system may be enabled for surgical use with the particular peripheral device 58 which has been calibrated. Should another peripheral surgical device be coupled to the system the calibration procedure must be repeated, unless that new peripheral surgical device had been previously calibrated within a predetermined period of time, programmed into the control circuitry. By use of this system one or more peripheral surgical devices may be calibrated prior to the performance of a surgical operation. Once calibrated, the various devices may be interchanged during the operation without recalibration.

When the peripheral surgical device is used in the surgical operations, manual controls such as the foot switch 204 and the switch panel 22 may be employed to control the operation of the laser system. The switch panel 22 may be used to manually select desired output power levels from the peripheral surgical device 58. Of course, during a surgical operation, the real power output of the peripheral surgical device 58 cannot be conveniently measured, since such a measurement would interfere with the operation. Instead, an approximation of the actual power output level of the peripheral surgical device 58 may be calculated from the stored ratio of power outputs produced in the calibration mode and from power levels continuously detected by the power detectors 100 and 102. A feedback circuitry may be provided as indicated by arrow 208 to control the operation of the laser, to thereby adjust the output beam 78 so that the desired set point power output level is achieved. The foot-switch 204 may be employed to control the timing and/or pulse duration of the laser beam used in the surgical operation.

A video display 20 may be connected to the control circuitry to provide a display of various operating parameters of the system such as tool identity, calculated device power output level, aiming beam power output level, calibration status of the peripheral device, etc.

FIG. 4 is a schematic illustration of modes of operation of the control circuitry of the laser system embodiment described in connection with the first three figures. In the Figure, the arrows show transitions or control flow between modes, indicated generally as circles. The operations indicated in FIG. 4 may preferably be performed in a general purpose digital computer with appropriate software.

The initial system mode, the system-off mode 300, represents the state of the system when no electrical power is being applied to the apparatus. The system may be placed in the laser-off mode 302 by unlocking a key lock system. In the laser-off mode, the control electronics are activated, and the system instructs the user to press an "on" button on the control panel. By so doing, the system may be placed in the on-power up mode 304, in which the laser is brought up to power. Once the laser has reached a predetermined power level, the system may pass into the calibrate mode 306, in which the system recalls the identity of any peripheral device which is presently calibrated and displays this information on the display screen. A peripheral device will remain in a calibrated state and calibration data retained in the electronic circuitry memory for a predetermined period following system shut-down, for example, eight hours. If the system determines that one or more peripheral devices are presently calibrated, the system may pass to the standby mode 308. Removal of the calibration pod will cause the system to return to the calibration mode 306. This is also true for modes 308 through 314, now to be discussed.

In the standby mode 308, desired power and pulse timing data for the main power and/or aiming beams can be entered and modified. This data is displayed on the display screen. Power values may be displayed which are calculated from the calibration ratio and a laser output power sensed internally in the system as discussed above. To go into the ready mode 310, a ready button may be pressed which activates the foot switch or other laser pulse initiating triggers.

In a preferred embodiment, the foot switch is provided with the capability of actuating two state or mode changes: light pressure on the foot switch places the system in the aim mode 312, in which an aiming beam is produced by the system; and greater pressure on the foot switch places the system in a full power mode 314 in which a power beam is produced. The system is designed so that it must be placed in the aim mode for a predetermined short interval before going to the full power mode. This arrangement inhibits the accidental triggering of the full power beam, for example, by dropping the foot switch or accidentally stepping on the foot switch.

The standby simmer mode 316 represents a lower power mode to which the system gravitates if the system has been in the standby or ready mode, but has not been used for more than a predetermined time interval.

The system may pass to a fault 2 mode 318 from a number of the other modes as shown. In response to the detection of a type 2 fault such as an interruption in electrical or optical connections to the peripheral device. In the fault 2 mode, the production of a laser pulse is inhibited. In such a case, if a calibrated peripheral device is then connected to the system, the system will return to the standby mode 308. If an uncalibrated peripheral device is connected to the system at this point, the system will pass to the calibration mode 306.

More serious problems such as a failure of the control circuitry or a cabinet interlock malfunction may cause the system to enter the fault 1 mode 320. As shown in FIG. 4, the system may pass from the fault 1 to the laser off mode 302. Correction of the type 1 fault must be effected before the system can be again be operated in the on-power up mode.

In preferred embodiments of the invention an optical-/electrical coupler is used to join the peripheral device to the laser and complete the electrical circuit necessary to give the the signature signal. FIG. 5 illustrates one form of socket 160 which can participate in this coupling and generation of a signature signal. This socket 160 is shown attached to the chassis of the coupler by bolts 36. Socket 160 includes a round socket aperture 37 with slots or detents 38 and 39 for latching and holding the plug when it is inserted. These slots or detents are of different size or positioned differently so that the plug can only be inserted and locked in one particular rotational orientation. In the center of the socket is an axially positioned laser output aperture 40 that is aligned to receive the output of the laser and pass it to the plug connector when it is latched into place.

Socket 160 additionally contains a plurality of contact points 41a, 41b, etc. In the embodiment shown, there are twelve such points but this number can be increased or decreased as desired. These contact points are positioned in alignment with engagement devices on plug 27 such that when plug 27 is locked into socket 160 a particular combinatio of these contact points are engaged. If the particular combination of points engaged is different for each of several plugs, this can provide an unambiguous identification signal or signature for the device attached by the plug.

The nature of the engagement between the contact points and the engagement devices is usually an electrical connection, either by a conductor or by a capacitance. However, it could be a purely physical engagement, which could have the effect of activating switches within socket 160, for example. Similarly, it could be an optical engagement in which one or more reflected light beams are detected at particular contact points and not at others.

In any of these embodiments it is essential that the means for effecting this signature within the plug portion of the connection be of minimal cost and complexity so as to permit the plug portion of the connector to be disposable. Thus, the electrical contact within the plug portion is preferably one or more conductors or shunts bridging a plurality of points so as to merely direct an electrical signal from some contact points in the socket back to a particular combination of other contact points in the socket.

Such a plug is shown in FIG. 6. In FIG. 6, plug 27 is shown including axially positioned light fiber 26 having fiber end 28. Plug 27 includes cylindrical plug body 42 having latching tabs 44 and 45 on its outside surface. Body 42 and tabs 44 and 45 are sized and positioned to insert into socket 160 and lock therein in one particular orientation in a twist-lock plug type action. Plug 27 also carries two conductor bars 46 and 47 in the face of its inside end. These bars are adapted to bridge two or more of contact points 41a, 41b, ect. in socket 24. The position of bars 46 and 47 around the circumference of plug 27 relative to locating tabs 44 and 45 is strictly controlled so as to provide precise bridging of particular patterns of contact points and thus create an unabiguous electrical circuit when the plug is inserted in the socket.

Contacts 41A etc. are connected to the control circuit. One method for doing this employs flexible circuit board 54 which can be located in coupler 18. The signature of a device can be determined from the circuit created by the connecting strips. One such method can employ the circuit shown on the flex circuit mask shown in FIG. 7. In this FIG., points 41a, etc. correspond to contacts 41a etc. Points 41b, c, f, g, i, and j are interconnected to common line while the remaining points connect to particular resistors $R_1$, $R_2$, $R_3$, $R_1'$, $R_2'$, and $R_3'$. Depending upon which of these resistors are selected, line 60 is coupled to one or both of lines 61 and 62 through one or two of these resistors. If desired, additional contacts could be bridged to create additional resistance variations. The specific resistance values thus created can be used by the laser control circuit to display information identifying the peripheral and or setting proper power output, and the like.

Figure 8:
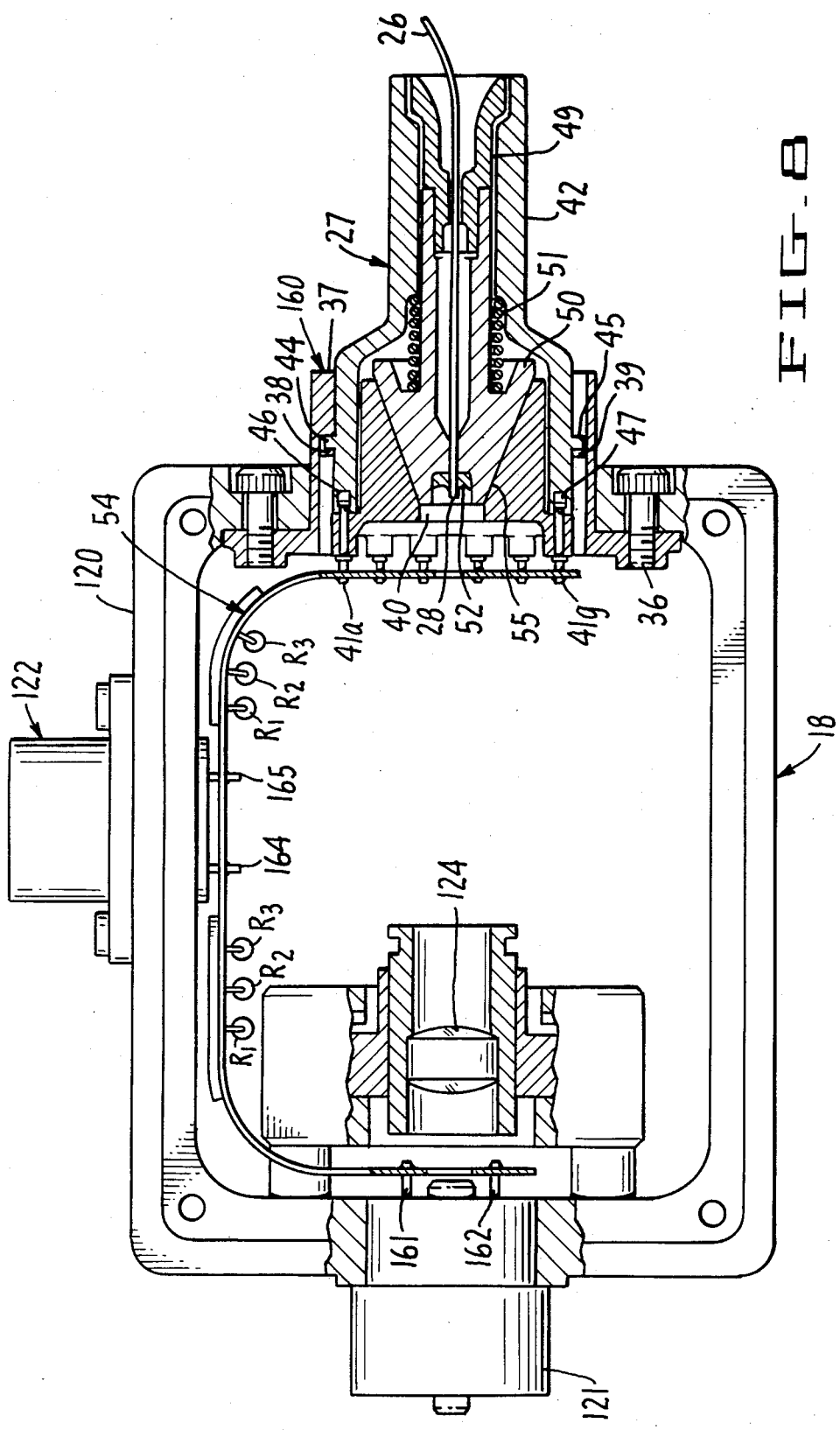
FIG. 8 is a sectional view of one type of optical/electrical coupler which can incorporate the socket of FIG. 5 and circuit of FIG. 7 to join to plug of FIG. 6 and facilitate the coupling of interchangeable peripherals, a preferred aspect of the invention.

Finally, turning to FIG. 8, optical coupler 18 shown in FIG. 1 is described in detail. It serves to connect the optical fibers and the electrical portions of the system. Coupler 18 as shown in FIG. 8 includes a housing 120 which carries input socket 121, laser output socket 160, and auxiliary electrical output connector 122. Input 121 and output 160 are located on the same optical axis. A beam of laser light entering the box from connector 24A through 121 is focused by lens 124 onto fiber optic end 28. Lens 124 is alignable by the system shown.

Socket 160 is attached to box 120 by screws 36 and contains socket body 37, latching slots 38 and 39, laser output aperture 40 and contact points 41a and 41g. Plug 27, carrying fiber optic 26 having input end 28 axially positioned in its center is held into a particular orientation by tabs 44 and 45 latched into slots 38 and 39. Contact strips (conductive shunts) 46 and 47 are shown in contact with 41A and 41G. Although not shown, it will be appreciated that each strip bridges to another contact so as to create an electrical circuit.

Other features of the plug are shown by FIG. 8. Optical fiber 26 passes through guide 49 which is press fit into axial positioner 50. The combination of guide 49 and positioner 50 floats within plug body 42 and is held in tension by compression spring 51. The taper of positioner 50 matches a taper 55 in socket 24 and when engaged compresses spring 51 so as to assure a tight engagement. The inner end 28 of optic fiber 26 is held in position by ceramic cement 52. This cement is formulated as a settable paste including a refractory. It is white in color so as to minimize absorption of laser energy. It prevents the laser from heating the plug, melting it, or causing it to vaporize and interfere with the transmission of laser output.

The circuit created when plug 27 is latched into socket 160 may be carried on flex circuit 54 and may, in one preferred embodiment incorporate, one or more resistors, $R_1$ etc. Flex circuit 54 continues to electrical imput plug 121 where, via pins 161 and 162 the signal is passed to connector 24a, for transmission to the control circuit

What is claimed is:

1. (Amended) An interchangeable laser surgical peripheral device comprising a directional plug of predetermined fixed orientation adapted to be connected to a laser output device; and axially affixed therein and extending therefrom a centered, flexible, laser light transmissive elongated optic fiber, the plug end of which is aligned to receive the output of the laser and the distal end of which is to be used for effecting the laser surgery procedure, said plug comprising means for providing a signature signal which distinguishes the particular peripheral device from other interchangeable peripheral devices when connected to the laser output in its predetermined fixed orientation.

2. The device of claim 1 wherein the signature signal which is provided when the device is connected to the laser output is an electrical signature signal.

3. The device of claim 2 wherein the plug contains means for unambiguously selecting an electrical circuit when it is connected to the laser output.

4. The device of claim 3 wherein said means for unambiguously selecting an electrical ciuruit comprises means for creating an unambiguous electrical circuit.

5. The device of claim 4 wherein said means for creating an unambiguous electrical circuit comprises means within said plug positioned to effect a preselected electrical contact bridge in the laser output device.

6. The device of claim 5 wherein said means for creating an unambiguous electrical circuit comprises means within said plug positioned to effect at least one preselected electrical contact bridge in the laser output device.

7. The device of claim 6 wherein the unambiguous electrical circuit created when the at least one preselected electrical contact bridge is effected is a selection of resistances.

8. The device of claim 4 wherein said means for creating an unambiguous electrical circuit comprises a conductor within said plug positioned to bridge preselected electrical contacts in the laser output device.

9. The device of claim 8 wherein said means for creating an unambiguous electrical circuit comprises at least one conductor within said plug positioned to bridge at least one pair of preselected electrical contacts in the laser output device.

10. The device of claim 9 wherein the unambiguous electrical circuit created when the at least one pair of preselected contacts is bridged is a selection of resistances.

11. The device of claim 10 wherein the directional plug is a twist lock plug.

12. The device of claim 11 wherein the plug end of the flexible, laser light transmissive elongated optic fiber is held in centered alignment by means comprising a laser energy resistive ceramic cement.

13. The device of claim 4 wherein the directional plug is a twist lock plug.

14. The device of claim 1 wherein the directional plug is a twist lock plug.

15. The device of claim 1 wherein the plug end of the flexible, laser light transmissive elongated optic fiber is held in centered alignment by means comprising a laser light resistive ceramic cement.

16. In a surgical laser apparatus comprising:
a laser operable to produce an output beam at an adjustable power level;
interchangeable peripheral surgical devices, a selected one of which is operatively coupled to the laser to receive the laser beam, said devices each having an identifying signature for use in identifying the selected device;
sensor means sensing the power output of a surgical device coupled to the laser; and
control circuit means operatively coupled to said sensor means and to the signature of the coupled device for (a) identifying the surgical device by means of the device's signature, (b) enabling the laser to produce an output beam when the surgical device is coupled to the sensor means for measuring the power output from the device, and (c) disabling the laser from producing an output beam for surgical use until the power output of such surgical device has been measured, the improvement comprising means for providing the signature of the peripheral device, said means being external to the peripheral but joined into an unambiguous signature circuit when the peripheral device is coupled to the laser.

* * * * *